(12) United States Patent
Barenholz et al.

(10) Patent No.: US 7,048,943 B2
(45) Date of Patent: May 23, 2006

(54) CAROTENOID-LOADED LIPOSOMES

(75) Inventors: Yeckezkel Barenholz, Jerusalem (IL);
Dvorah Diminsky, Jerusalem (IL);
Rivka Cohen, Jerusalem (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 0 days.

(21) Appl. No.: 10/073,365

(22) Filed: Feb. 13, 2002

(65) Prior Publication Data

US 2003/0059462 A1    Mar. 27, 2003

Related U.S. Application Data (60) Provisional application No. 60/268,185, filed on Feb. 13, 2001.

(51) Int. Cl.
*A61K 9/127* (2006.01)

(52) U.S. Cl. .................. 424/450; 264/4.1; 264/4.3; 514/725

(58) Field of Classification Search ................ 424/401, 424/450; 264/4.1, 4.3; 514/725
See application file for complete search history.

(56) References Cited

U.S. PATENT DOCUMENTS

| 4,192,859 A | * | 3/1980 | Mackaness | |
| 5,034,228 A | | 7/1991 | Meybeck et al. | |
| 5,700,482 A | * | 12/1997 | Frederiksen et al. | ........ 424/450 |

FOREIGN PATENT DOCUMENTS

| EP | 0 229 561 B1 | 8/1992 |
| FR | 2 664 164 A1 | 1/1992 |
| WO | WO 94/13265 A1 | 6/1994 |

OTHER PUBLICATIONS

Stahl, W., FEBS Letters, 427, pp. 305-308, 1998.*
DATABASE WPI, Section Ch, Week 200131, Derwent Publications Ltd. London, GB; AN 2001-293982 & JP-A-2001 002566.

* cited by examiner

*Primary Examiner*—Gollamudi S. Kishore
(74) *Attorney, Agent, or Firm*—Browdy and Neimark, PLLC (57) ABSTRACT

The present invention is based on a novel method for encapsulating in liposomes substantially water immiscible carotenoids. Therefore, there are provided by the present invention formulations comprising liposomes loaded with an amount of at least one water immiscible carotenoid, pharmaceutical compositions comprising such a formulation, and a method for preparing the liposomes loaded with said carotenoid.

24 Claims, 2 Drawing Sheets

■ 0 MED
▨ 7 MED
▨ 11 MED

CAROTENOID-LOADED LIPOSOMES

FIELD OF THE INVENTION

This invention relates to liposomal formulations containing as active ingredient one or more carotenoid.

BACKGROUND OF THE INVENTION

The therapeutic function of long-chain, highly unsaturated carotenoids of higher plants is becoming increasingly well understood. The conjugated polyene chromophore of such molecules determines not only the carotenoids light absorption properties, and hence color, but also the photochemical properties of the molecule and consequent light harvesting and photoprotective action. The polyene chain is also the feature mainly responsible for the chemical reactivity of carotenoids towards oxidizing agents and free radicals, and therefore for any antioxidant function.

Carotenoids having the above described features, include but not limited to, lutein, zeaxanthin, beta carotene and lycopene.

Lycopene is an open-chain unsaturated carotenoid that confers red color to tomatoes, guava, rosehip, watermelon and pink grapefruit. This compound is non-polar and lacks any type of interaction with water. Thus, when introduced into water, it forms granules. Lycopene exhibits the highest physical quenching rate constant with singlet oxygen and its plasma level is slightly higher than that of beta carotene. Epidemiological evidence revealed that lycopene and the like exert a protective action against certain types of diseases, including cancer, heart disease and other diseases which have radical or oxidant involvement.

One of the major difficulties in formulating carotenoids is their lack of solubility and homogenous dispersibility in water and low solubility in many organic solvents. The low solubility of carotenoids which is related to their high lipophilicity and rigid structure, leads to low bioavailability of the compound. It is thus suggested by the present invention to make use of liposomal delivery systems to improve the bioavailability of carotenoids.

It has well been established that liposomes are suitable delivery vehicles for parenteral, peroral, topical and inhalation administration of drugs. Liposomes, which are biocompatible, may improve for an active substance the formulability, provide prolonged release, improve the therapeutic ratio, prolong the therapeutic activity after each administration, reduce the need for frequent administration, reduce the amount of drug needed and/or absorbed by target tissue.

Active substances, such as drugs, may be contained within the liposome (in the intraliposomal aqueous phase) or entrapped within the lipid bilayer. In the later case, the drug may be positioned parallel to the acyl chains or in the bilayer center. Further, the active substance may be bound to the outer surface of the liposome.

Loading of drugs into liposomes has proved to be a measure of their utility. If there is a poor loading, there is a great loss of the active drug and the use of the liposomes as the pharmaceutical vehicle becomes uneconomical.

SUMMARY OF THE INVENTION

The present invention is based on a new method for preparing a bioavailable formulation containing water immiscible carotenoids.

Thus, according to a first of its aspects, the present invention provides formulations comprising liposomes loaded with an amount of at least one carotenoid being immiscible in water.

The term "loaded" as used in connection with the liposomal formulation of the invention refers to the location of the carotenoid with respect to the liposome. Accordingly, the liposome may be contained within the intraliposomal phase, or entrapped within the lipid bilayer. In the latter case, the carotenoid may be parallel to the acyl chains or enclosed within the lipid bilayer's center.

The term "immiscible in water" means that the carotenoid has substantially no or statistically non-significant solubility in water.

The invention also concerns pharmaceutical compositions comprising liposomes loaded with an effective amount of at least one carotenoid substantially immiscible in water and a pharmaceutically acceptable carriers, excipients etc., The term "effective amount" for the purposes described herein is that determined by such considerations as are known to those versed in the art. The amount of the carotenoids carried by the liposomes must be sufficient to achieve a desired therapeutic effect, e.g. to treat, prevent or ameliorate symptoms associated with a disease against which the carotenoids is effective, to lessen the severity or cure the disease or to prevent the disease from occuring. Particularly, the effective amount of the carotenoid is such that it acts against the harmful effects of undesired oxidation of lipids, proteins, tissues or cells, in the living body, for example, by environmental hazards, which can exert damage. Such environmental hazards include UV radiation or oxidative agents.

The term "damage" is to be understood as any damage resulting from a variety of oxidative agents such as oxygen itself, hydroxyl radical, hydrogen peroxide, other free radicals, ozone, etc., or from any kind of harmful UV irradiation, such a UVA and UVB irradiation. The damage would depend upon the target for which the preparation is used. Thus, if the preparation is used on skin, damage may be any skin damage such as burn, blisters, damage appearing after chronic exposure to sun, e.g., premature aging of the skin, etc.

The composition of the present invention is preferably for topical application or for oral administration, and preferably includes, as its active ingredient lycopene.

The invention also provides a method for the preparation of a formulation comprising liposomes loaded with an effective amount of at least one carotenoid substantially immiscible in water, the method comprises the steps of:

(i) dissolving a powder of liposome-forming lipids in an organic solvent to a level close to saturation;

(ii) adding to the solute of step (a) at least one dry, water immiscible carotenoid to obtain a suspension, drying the same to obtain a second dry powder;

(iii) dehydrating the second dry powder in an aqueous solution to yield the carotenoid containing liposomal formulation.

The term "liposome-forming lipids" use herein refers to lipids, preferably amphipathic lipids which contain groups with charateristically different properties, e.g. both hydrophilic and hydrophobic properties, which upon dispersion thereof in an aqueous medium for vesicles (liposomes). The liposome-forming lipids may include a single type of lipids or a mixture of two or more lipids. The lipids may also be modified lipids, including PEGylated lipids an according to one preferred embodiment include unsaturated lipids.

According to a further of its aspects, the invention provides a therapeutic method for the treatment of damage caused by oxidation or exposure to UV light resulting in the formation of singlet oxygen, he method comprises providing an individual in need a formulation comprising liposomes loaded with an effective amount of at least one carotenoid substantially immiscible in water.

The term "treatment" as used herein refers to administering a therapeutic amount of the formulation of the present invention effective to ameliorate at least some of the undesired symptoms associated with a disease caused by oxidation of exposure to UV light, to prevent the manifestation of such symptoms before they occur, down the progression of a disease, enhance the onset of remission periods (if any), slow down any irreversible damage caused by the disease, lessen the severity or cure the disease, or prevent the disease form occurring, as well as to the prevention of such damage or of diseases or disorders caused by the same.

DETAILED DESCRIPTION OF THE INVENTION

The present invention is based on the surprising finding that lycopene, a highly lipophilic carotenoid having a rigid structure, can be homogeneously mixed with phospholipids at more than expected relatively high mole ratio, thereby forming multilamellar liposomal vehicles (MLV) comprising the carotenoid.

Thus, according to a first of its aspects, the present invention provides a formulation comprising liposomes loaded with an effective amount of at least one carotenoid, the carotenoid being immiscible in water.

The liposomal formulation of the invention may be formulated to be in a dosage form for use for pharmaceutical purposes, cosmetic purposes or as a food additive.

The ratio between the carotenoid and the lipids in the liposomal formulation may vary widely and is preferably within the range of about between 1:1 and 1:500.

The carotenoid is preferably an antioxidant, and more preferably a molecule having singlet oxygen quenching and peroxyl radical scavenging characteristics. Therefore, the formulation of the present invention is in fact an anti-oxidant formulation, and the composition of the invention is for the treatment or prevention of damages caused by undesired radiation.

According to one embodiment, the antioxidant is lycopene. Lycopene is known to posses, inter alia, the above described chemical properties and thus is one of the preferred carotenoids employed by the present invention. There are several types of lycopene depending on the purity of the substance produced from tomatoes. In the following description reference is made lycopene 75% (71.9% purity), lycopene 92% (92% purity) and lycopene 95% (95% purity). However, it should be understood that these types of lycopenes are mere examples and the invention should not be limited to lycopene 75%, lycopene 92% or lycopene 95%.

Other water-immiscible carotenoids which may be used in the formulation of the present invention include 4,4'-diketocarotenoid, astaxanthin, canthaxanthin, zeaxanthin, beta-cryptoxanthin, lutein, 2', 3'-anhydrolutein, B-carotene and rubixanthin, all of which are known to have scavenging and anti-oxidizing activity.

The liposome-forming lipids utilized by the present invention are preferably but not limited to pliospholipids. According to one embodiment of the present invention, the phospholipids are derived from egg yolk phospholipids (EPL) enriched with phosphatidyl choline (EPC), whereas, according to another embodiment, the phospholipids are derived from soy beans (soyphospholipids, SPL).

As will be described hereinafter, several types of EPL- or soy bean-derived lipids are used in the formulations of the present invention. One preferred phospholipid is referred to by the name E-100, which is in fact a phospholipid composed of 96% phosphatidylcholine (PC) produced from EPL. Another preferred phospholipid is S-45, which is composed of 45% PC produced from SPL. Accordingly, other EPL or SPL derived lipids can be employed, some of which are described in the following specific Examples and include S-20, S-20N and S-35, all of which are known to those versed in the art.

The composition of the present invention may further include pharmaceutically acceptable additives, food additives and any other physiologically acceptable additive. By the term "pharmaceutically acceptable additives" it is meant any substance added to the liposomal formulation for a specific purpose. Such additives may include diluents or carriers to give a form or consistency to the formulation when it is given in a specific form, e.g. in pill form, as a simple syrup, aromatic powder, and others.

The additives may also be substances for providing the formulation with stability (e.g. preservatives) or for providing the formulation with an edible flavor e.g. honey, mayonnaise).

Preferably, the additives are inert non-toxic materials, which do not react with the carotenoid. Nevertheless, the additive may also be an adjuvant, which, by definition, are substances affecting the action of the active ingredient in a predictable way.

Further, the formulation of the invention may also include other biologically functionally substances, such as vitamin A, vitamin E, etc.

Yet further, the composition of the present invention may include a combination of one or more carotenoid and other antioxidants, such as vitamin C, vitamin E, beta carotene (provitamin A), selenium, glutathione, cysteine, uric acid or synthetic antioxidant like DMSO, BHT, BHA and nitroxides. These additional anti-oxidants may either be entrapped in the lipid bilayer encapsulated within the liposome or be adhered to the surface of the liposome.

According to one embodiment, the composition of the present invention is applied topically to the skin of a subject, in which case, the composition is preferably in the form of a cream, a lotion or a hydrogel preparation. Formulations for topical application may further comprise physiologically acceptable aromatic substances to provide the formulation with a pleasant odor. As will be disclosed in the following Examples, when the formulation was applied onto an epidermal equivalent, protection of the equivalent against UV irradiation was achieved. Thus, the formulation of the present invention, when formulated for topical application, may be used to protect an individual from damages caused by exposure to UV radiation.

According to another embodiment, the formulation of the present invention may be administered orally to an individual in need thereof. In this case, the formulation may be contained in a capsule or be in the form of an edible liquid, e.g. suspension, syrup and the like. Such formulation may be useful for protection against damage caused by systemic oxidative agents.

The formulation for oral administration may be manufactured and provided in the form of a powder, which, just before administration, is dispersed in a suitable liquid, e.g. water, to yield the edible dispersion, for oral administration.

The formulation of the present invention has also other therapeutic utilities. Since the carotenoids are antioxidants and protectants against excessive radiation, the formulation of the present invention may be used against any chronic degenerative and/or progressive diseases caused by singlet oxygen. Singlet oxygen is formed by free radical chain reactions characterized by the interaction of radicals with oxygen to yield peroxy radicals, organic peroxides and the like. Such free radicals damage cell parts including cell membranes, nuclear membranes, DNA, cell membrane fats and proteins. The damage caused results in the formation of numerous chronic degenerative and progressive diseases including, inter alia, cancer (e.g. cancer of the digestive tract, breast and prostate cancer, etc.) heart related diseases (i.e. cardiovascular disorders) diseases related to the immune system (e.g. Multiple Sclerosis, Lupus, Scleroderma, AIDS), neurodegenerative diseases (e.g. Alzheimer and Parkinson's), skin wrinkling, aging and the formation of cataracts. Thus, it is to be understood that the formulation of the present invention may be useful against a wide range of damages, disorders and diseases caused by singlet oxygen, and it is thus to be understood that the present invention also provides a formulation for the treatment of disorders caused by singlet oxygen.

The present invention also concerns a method for the preparation of a liposomal formulation comprising, at least one carotenoid substantially immiscible in water, the method comprising the steps of:
(i) dissolving a powder of liposome-forming lipids in an organic solvent to a level close to saturation;
(ii) adding to the solute obtained in (a) at least one dry, water immiscible carotenoid to obtain a suspension and drying the same to form a second dry powder;
(iii) rehydrating rehydrating the second dry powder in an aqueous solution to yield the carotenoid-containing liposomal formulations The water immiscible carotenoid and the lipids employed for the formation of the liposomal formulation of the present invention are as defined hereinbefore. The weight ratio between said carotenoid and the liposome-forming lipids in the formulation obtained is preferably in the range of between about 1:1 and about 1:500, wherein the carotenoid is preferably lycopene.

According to one preferred method of the present invention, cyclohexane is used as the organic solvent. As further detailed hereinafter, cyclohexane is a preferred solvent as it has a relatively high freezing temperature, and high vapor pressure which enables its easy and fast removal from the formulation upon lyophylization or freeze drying of die suspension, leaving behind a porous dried cake. The aqueous solution may be any edible aqueous solvent, however, is preferably water. Nevertheless, tertiary butanol, capable of dispersing therein lycopene, may also be employed by the method of the present invention.

The present invention further relates to a method for the treatment of damage caused by singlet oxygen, the method comprises the step of providing to an individual in need a formulation comprising liposomes loaded with an effective amount of at least one carotenoid substantially immiscible in water. The formulation may be provided to the individual for therapeutic or cosmetic purposes, or as a food additive.

The liposomal formulation or composition of the present invention is administered and dosed in accordance with good pharmaceutical practice, taking into account the conditions of the treated individual, the site and method of administration, scheduling of administration, subject's age, sex, body weight and other factors known to those in the art of pharmaceutics. The liposomal formulation or composition can be administered in various ways. According to one preferred embodiment, the carotenoid-loaded liposomes of the present invention are formulated for topical applications for therapeutic or cosmetic treatment. To this end, the liposomal formulation obtained by the method of the invention described above is further mixed with physiologically acceptable carriers to obtain a cream, a lotion, an ointment, a gel, a hydrogel and the like, suitable for topical application, as known to hose skilled in the art.

According to a further embodiment, the carotenoid-loaded liposomes of the present invention are provided orally to the individual in need of the same. To this end, the liposomal formulation is combined with pharmaceutically acceptable carriers suitable for the formation of dosage forms, e.g. capsule, wherein the liposomes are contained therein, or in the form of an edible liquid, e.g. a suspension, a syrup, and the like.

Further, the carotenoid-loaded liposomes of the present invention may be formulated as an edible product, to be provided to an individual as a food additive.

According to yet a further aspect of the invention, there is provided a composition comprising dried liposome-forming lipids and at least one dried water-immiscible carotenoid, which upon mixing with an aqueous solution (e.g. water) yields liposomes loaded with said carotenoid, the dried carotenoid being in an amount to obtain in the thus formed liposomes a pharmaceutically effective amount of the carotenoid. The composition according to this aspect of the invention is preferably in the form of a dry powder and more preferably a lyophilizate.

The dry liposome-forming lipids and carotenoid are, respectively, those as defined hereinabove. These dry components may be obtained in various ways, for example, by dissolving separately the lipid/s and carotenoid/s in a suitable organic solvent (which may be the same or different) followed by removal of the solvent e.g. freeze drying and lyophylization.

Finally, the present invention provides a kit for the preparation of carotenoid-loaded liposomes, the kit comprising (1) dry liposome-forming lipids; (2) dry water-immiscible carotenoid; (3) sterile aqueous solution; (4) instruction for use of the dry lipids, the dry, water-immiscible carotenoid and the aqueous solution to yield carotenoid-loaded liposomes, and instructions for use of the loaded liposomes thus obtained.

Evidently, any other application wherein the use of a singlet oxygen scavenger is required forms part of the present invention. Those skilled in the art would know how to make use of the formulation of the present invention for other applications, which are not specifically mentioned or exemplified hereinbefore and after.

It is to be understood that both the foregoing general description and the following detailed examples are provided merely for the purpose of explanation and are in no way to be construed as limiting of the present invention.

SPECIFIC EXAMPLES

General Information

Materials

The following Table 1 summarizes the characterizing features of the materials employed in the following specific however, non-limiting, Examples. It should be noted that the commercial names of the substances used as liposome forming lipids indicate the percentage of phosphatidylcholine in the substance, e.g. S20 refers to 20% phosphatidylcholine in the mixture of lipids. In the same manner, S40 refers to 40%, S35 to 35% and E100 to 100% phosphatidylcholine in the mixture of lipids. The following examples, S20, S20N, S35, S40 and E100 are all products of Lipoid GmbH, Germany. The mixture of lipids in the liposomes forming lipids employed may include, in addition to the phosphatidylcholine, phosphatidyl ethanolamine, phosphatidyl inositol, or any other vesicle forming substances (e.g. oil, other lipids etc.).

TABLE 1

| Material | Source | Purity | Commercial name | Company |
|---|---|---|---|---|
| Lycopene 75 | Tomatoes | 71.9% | Lyco-Mato 70% | LycoRed[a] |
| Lycopene 95 | Tomatoes | 95.0% | Lyco-Mato 95% | LycoRed[a] |
| Phosphatidylcholine | Soy oil | | S-20 | Lipoid GmbH |
| Phosphatidylcholine[b] | Soy oil | | S-20N | Lipoid GmbH |
| Phosphatidylcholine[b] | Soy oil | | S-35 | Lipoid GmbH |
| Phosphatidylcholine[b] | Soy oil | | S-40 | Lipoid GmbH |
| Phosphatidylcholine[b] | Egg | | E-100 | Lipoid GmbH |
| Cyclohexane[c] | | 99.7% | | Bio-Lab |
| 2-methyl propan-2-ol | | 99.0% | tertbutyl alcohol | BDH |
| Ethanol[d] | | 99.8% | | Frutarom |
| 2-propanol[e] | | 99.8% | isopropanol | Bio-Lab |
| Methanol[c] | | | | Bio-Lab |
| Methylene chloride[c] | | | | Bio-Lab |
| Hexane[c] | | | | Bio-Lab |
| Acetonitrile[c] | | | | Labscan |
| Soy oil | | 100.0% | | Shemen |
| Deferoxamine[d] | | | Desferol | Ciba-Geigy |

[a]LycoREd natural products industrial;
[b]lechitin;
[c]for HPLC;
[d]analytical grade;
[e]powder Cell Culture Epidermal equivalents (4.0 cm²) were purchased from SkinEthic (Nice, France). Each equivalent served as a multilayered model of the epidermis consisting of normal, human-derived epidermal keratinocytes. Equivalents were cultured in a defined hydrocortisone and phenol red free medium supplied from SkinEthic.

Instruments

Kontron (Switzerland) HPLC system. 425 pump, 430 detector, 460 automatic injector and 450 data analysis system. Column: LiChroCART®250-4, RP-select B (5 µm), Merck catalog no. 1.50214

Size distribution processor analysis of the Coulter model N4SD Submicron Particle Analyzer (Coulter Ellectronics, Luton, England).

A5-6021 Flask shaker (St. John Associates, Inc. Battasville, Md., USA)

Hetolyophilizator, FD3, HetoHoltena/s, Denmark.

Ultrasonic Bath Transsonic 460/H Elma, Germany.

Methods

Lycopene Quantification—lycopene was analyzed for degradation and quantified by The HPLC buffer used comprised acetonitrile: methanol: methylene chloride: hexane and a ratio of 850:100:25:25 (all HPLC grade, Hoffman La Roche). Quantification was based on a standard curve obtained for lycopene (LycoRed standard. The amount of lycopene was also determined by absorbance at 472 nm.

Phospholipid Quantification—Total phosphorus was determined by the method described by Barenholz and Amselem [Barenholz and Amselem, Liposome Technology, Vol. 1, 2$^{nd}$ Edition, Liposome preparation and related techniques (Gregoriadis, G. Editor) CRC Press, Boca Raton Fla. Pp. 527–616, (1993)].

Particle Size Distribution—size distribution of MLV-entrapped lycopene was measured by dynamic light scattering (DLS) using the size distribution processor described hereinbefore.

Specific Preparations

Preparation of Formulation SO1

Content—Lycopene 75%:E-100, with a weight ratio of 1:45.

Method of Preparation—The phospholipids were dissolved in cyclohexane at a w/v ratio of 1 mg phospholipid per 10 ml cyclohexane. The dissolving required heating for several seconds at 60° C. and/or sonication for up to 3 minutes. Lycopene was added as powder to the solution, which was then vortexed. The resulting solution was lyophilized overnight and kept at −20° C. until use. To form multilamellar liposome (MLV), 2 ml of 0.9% NaCl were added to the lyophilizate followed by vortex to yield MLV encapsulated lycopene.

Preparation of Formulation SO2

Content—Lycopene 75%:E-100, with weight ratio of 1:10.

Method of Preparation—Lycopene was dissolved in cyclohexane at a w/v ratio of 1 mg of phospholipid per 10 ml of cyclohexane. The dissolving required heating at 60° C. for several minutes and sonication for up to 3 minutes. The E-100 phospholipids were added as powder to the solution and the mixture was vortexed. Then, the solution was fast frozen and lyophilized overnight and kept at −20° C. until use. To form multilamellar liposomes, 2 ml of 0.9% NaCl were added followed by vortexing to yield the MLV encapsulated lycopene.

Preparation of Formulation SO3

Content—Lycopene 75%:S-45, with weight ratio of 1:45.
Method of Preparation—Phospholipids were dissolved in cyclohexane at a w/v ratio of 1 mg per 10 ml of cyclohexane. The dissolving required heating for several seconds at 60° C. and/or sonication for up to 3 mins. Lycopene was then added as powder to the solution and the mixture was vortexed. The solution was lyophilized overnight, and kept at −20° C. until use. Total powder weight per bottle after lyophilization was 31.8 mg. To form MLV encapsulated lycopene, 2 ml of 0.9% NaCl were added followed by vortex.

Preparation of Formulation SO4.

Content—Lycopene 75%: S-45, with weight ratio of 1:45.
Method of Preparation—Lycopene was dissolved in cyclohexane at a w/v ratio of 1 mg of phospholipid per 10 ml of cyclohexane. The dissolving required heating for several seconds at 60° C. and/or sonication for up to 3 minutes. The phospholipids were added as powder to the solution and the mixture was mixed with vortex. The solution was lyophilized overnight, and kept lyophilized at −20° C. until use. Total powder weight per bottle after lyophilization was 31.8 mg.
To form MLV encapsulated lycopene, 2 ml of 0.9% NaCl was added followed by vortex.

Preparation of Formulation E1

Content—Lycopene 75%:E-100, with weight ratio of 1:10.
Method of Preparation—Lycopene was dissolved in cyclohexane at a w/v ratio of 1 mg of lycopene per 2 ml of cyclohexane. The dissolving required heating for several seconds at 60° C. and sonication for up to 3 minutes until all the lycopene was dissolved. The phospholipids were added as powder to the solution and the mixture was mixed with vortex. The solution was lyophilized overnight in bottles and closed in vacuum. The lyophilized bottles were kept at −20° C. until use.
To form MLV encapsulated lycopene, 2 ml of 0.9% NaCl were added followed by vortex. The percentage of entrapment of lycopene in the formulation was 85.31%.

Preparation of Formulation E2

Content—Lycopene 75%:E-100, with weight ratio of 1:10 and Desferal.
Method of Preparation—the method of preparing formulation E2 is the same as for formulation E1, however, also including Desferal. Desferal (100 μM dissolved in saline) was added to the mixture of Lycopene 75% and E-100 before fast freeing and lyophilization. The percentage of entrapment of lycopene in the formulation was 85.31%.

Preparation of Formulation E3

Content—Lycopene 75%:E-100, with a weight ratio of 1:20.
Method of Preparation—Formulation E3 was prepared according to the steps described in connection with formulation E1, except for the dissolution ratio. The present preparation, every 1 mg lycopene was dissolved in 4 ml of cyclohexane. The percentage of entrapment of lycopene in the formulation was 97.84%.

Preparation of Formulation E4

Content—Lycopene 75%:E-100 with a weight ratio of 1:20, further including Desferal.
Method of Preparation—Formulation E4 was prepared according to the steps described in connection with formulation E3. Desferal (100 μM dissolved in saline) was added to the mixture of lycopene and E-100 before fast freeing and lyophylization. The percentage of entrapment of lycopene in the formulation was 98.27%.

Preparation of Formulation E5

Content—Lycopene 75%:E-100, with weight ratio of 1:30.
Method of Preparation—Formulation E5 was prepared according to the steps described in connection with formulation E3. The percentage of entrapment of lycopene in the formulation was 87.67%.

Preparation of Formulation E6

Content—Lycopene 75%:E-100 with weight ratio of 1:30, further comprising Desferal.
Method of Preparation—Formulation E6 was prepared according to the steps described in connection with formulation E3. Desferal (100 μM dissolved in saline) was added to the mixture of Lycopene 75% and E-100 before fast freeing and lyophilization. The percentage of entrapment of lycopene in the formulation was 96.73%.

Preparation of Formulation E7

Content—Lycopene 75%:E-100, with weight ratio of 1:50.
Method of Preparation—Formulation E7 was prepared according to the steps described in connection with formulation E3. The percentage of entrapment of lycopene in the formulation was 100%.

Preparation of formulation E8

Content—Lycopene 75%:E-100 with weight ratio of 1:50, further comprising Desferal.
Method of Preparation—Formulation E8 was prepared according to the steps described in connection with formulation E3. Desferal (100 μM dissolved in saline) was added to the mixture o Lycopene 75% and E-100 before fast freeing and lyophylization. The percentage of entrapment of lycopene in the formulation was 100%.

It should be noted that as lycopene is sensitive to light, all bottles containing the above-described formulations were protected with aluminum foil paper. Further, lycopene is sensitive to air oxidation, thus, it was essential to prepare the formulations as quickly as possible. All preparations were performed in an ice bucket, to keep the mixture temperature at 4° C.

Photoprotection Analysis

Each formulation (500 μl) was topically applied to the surface of the epidermis model (hereinafter referred to as the 'treated epidermal equivalent'), 1 hour prior to UV irradiation. UV irradiation was performed with a solar spectrum Fluorescent Sunlamp (FS) in an exposure chamber. The treated epidermal equivalents received 0, 7 and 11 MED of solar spectrum light.

Twenty four hours post irradiation, the culture medium was collected from the treated epidermal equivalents and evaluated for IL-1α release levels using a commercially available ELISA kit. Cell viability was determined immediately post irradiation using LDH leakage measurments.

RESULTS AND DISCUSSION

Solubility

The solubility of lycopene 75% in various organic solvents is presented in the following Table 2. All samples were diluted with ethanol before measurement. The saturation concentrations of the lycopene were determined by BPLC and by the use of a spectrophotometer (absorbance at 472 nm, where the area under the peak was measured). The saturation limit was defined as the concentration where a precipitate first appears. The concentration of lycopene at saturation was determined after removal of precipitate by high speed centrifugation from the absorbance at 472 nm (the $\lambda$max for the 'red' form of lycopene) using double beam UVikon 860 (Kontron, Switzerland) spectrometer. The color of die suspension examined and the percentage of the degradent detected by HPLC (at 472 nm) are also indicated in the following Table 2.

TABLE 2 solubility of lycopene 75% in organic solvents

| Solvent | Color | Concentration (mM)/HPLC | Concentration (mM)/spectro. | % degredant |
|---|---|---|---|---|
| Cyclohexane | light red | 0.22 | 0.299 | 4.06 |
| t-butanol | light orange | 0.016 | 0.031 | 5.82 |
| i-propanol | light orange | 0.037 | 0.023 | 6.8 |
| ethanol | orange | 0.059 | 0.03 | 4.27 |
| Soy oil | dark red | 0.14 | 0.139 | 2.73 |
| n-hexane | Orange/red | 0.18 | | |

Cyclohexane was found to be the most effective solvent for lycopene.

The maximal solubility in cyclohexane of the phospholipids employed herein was also determined. Table 3 summarized the saturation concentrations of these lipids.

TABLE 3

Solubility of lipids in cyclohexane

| Phospholipid | Solubility (gr. lipid in 100 ml cyclohexane) | mmole/L cyclohexane |
|---|---|---|
| S-40 | 70 | 427.15 |
| S-20 | 50 | 355.32 |
| S-20N | 20 | 146.87 |
| S-35 (liquid) | 100 | 286.76 |
| E-100 | 45 | 302.54 |

From the values presented in Tables 2 and 3 it was concluded that cyclohexane should be the solvent of choice for further processing. Cyclohexane has also a high freezing temperature ~6° C., and high vapor pressure which allows its easy removal from solutions upon lyophilization. The saturation concentration of the mixture of lycopene and the lipids was determined by the Lycopene concentration, at the point where a precipitate first appeared. Bach concentration was determined according to the quantification methods described above, after removal of the initial precipitate by centrifugation.

The lipids' solubility in cyclohexane showed no dependence on the degree of purity of the lipid. Maximizing the solubility of the lipid was essential in order to minimize the amount of solvent and time required for lyophylization of the formulation.

The order of solubility obtained for the lipids was as follows: S-45>S-20>E-100>S-35>S-20N.

Lycopene's solubility was determined for lycopene 75% (Table 2) and lycopene 95%. Both types of lycopene were in a powder form before dissolving in cyclohexane. The maximal solubility of lycopene 95% in cyclohexane was found to be 2.65 mM, whereas, the solubility of lycopene 75% in the same solvent was 1.96 mM. These measures were taken after a year and a half of storage at −20° C.

The homogeneity of the lycopene powder was also an important feature as it showed the unexpected results of homogenous distribution of lycopene in PC preliposomal powder. This is an indication that no macroscopic phase between the two components of the formulation occurred. This feature was also quantified by taking different aliquots of the dry lycopene/PC powder from several different regions of the dry cake and measuring the lycopene and PC composition per mg powder and calculating therefrom the mole ratio between the two components. This mole ratio is an indication of the level of homogeneity. The results revealed that there is no macroscopic phase separation induced by saturation, which is directly related to the input ratio between these two components.

In addition, the homogeneity of the lycopene powder was not affected by the order of addition of the two components into the cyclohexane. A change in the color of the lycopene (yellow, pink or red) was observed. Nonetheless, this change has no necessarily correlation with the lycopene content in the formulation.

Liposome—Encapsulated Lycopene

Lycopene 75% and lycopene 95% were encapsulated in MLV, with several different lipid/lycopene weigh ratios, including 1:1, 5:1, 10:1 and 45:1. The liposomes (MLV) were prepared as described hereinbefore.

In general, the population of the liposomes was heterogeneous. Most of the liposomes-containing lycopene 75% had a mean size of 2.0–3.9 μm and a small fraction of liposomes had a mean size of 0.3–0.7 μm. Re-suspension with double distilled water (DDW) of powders containing a lipid and lycopene 95% in weight ratio of 1:1 and 1:5 resulted in the formation of large liposomes (mean size of 10 μm) and visible aggregates of lycopene. Up to 6% of these liposomes population had a mean size of 0.8–1.0 μm. Ultra-sonication of these liposomes for 6–10 minutes eliminated most of the aggregates in the suspension and reduced the size of liposomes to 5.5 μm and smaller. Sixty eight percent of the liposomes composed of lipid/lycopene 95% with a weight ratio of 10:1 had a mean size of 3.1 μm, and the rest had a mean size of 0.8 μm without sonication. The 75% lycopene entrapment in liposomes composed of lipid/lycopene 10:1 was measured, wherein 17.5% of the lycopene was entrapped in the MLV. Encapsulation of lycopene 75% or lycopene 95% in MLV composed of EPC/lycopene ratio of 10:1. 5:1 or 1:1 revealed, in general, that the increase in the phospholipid/lycopene ratio increased the percentage of encapsulation of lycopene in the MLV.

Encapsulation of lycopene 75% or lycopene 95% in small unilamellar liposomes (SUV) composed of a lipid/lycopene weight ratio of 1:10, 1:5 or 1:1 correlated with the amount of lycopene encapsulation in the MLV.

The partition coefficient of lycopene in tri-phase systems was also evaluated. Tri-phase systems may serve for the determination of availability of the lycopene into biological membranes. The system used herein was composed from two phases: soya oil in which the lycopene was present and water in which liposomes (10% by weight) in the form of small unilamellar vesicles (SUV) composed of pure egg phosphatidyl choline are present as the third phase.

The small unilamellar liposomes (SUV) composed of pure lipid (Ludwigshafen, Germany) egg phosphatidylcholine (egg PC) of an 80 nm were prepared and characterized as described by Haran et al. [Haran G. et al. Biochim. Biophys. Acta 1151:201–215 (1993)]. SUV egg PC size was ~80 nm. The partition coefficient in the three phase system was performed at three different levels of lycopene—low, medium and high amounts, using crystalline lycopene (originated from fungi), 92% powder (LycoRed), 75% powder lycopene (LycoRed) and oleoresin (containing 6.06% by weight of lycopene). In case of the highest level, lycopene from tomato concentrate (containing 0.073% lycopene) was also evaluated.

Preparation of the three phase systems included the following steps; first, lycopene was dispersed in soya oil (4 ml) by ultrasonic irradiation in an ultrasonic bath (35 kHz, 285W). Then, the precipitate was removed, aliquots of the oil were diluted in isopropanol with ratio ranging from 1:10 to 1:100 and the concentration of lycopene in oil phase was determined.

Then, to soya oil saturated with lycopene (1.5 ml) egg PC SUV in water (1.5 ml) were added to form the three phase system. The system was then mixed for 2 hours at room temperature using a flask shaker (A5-6021, St. John Associate Inc.), after which aliquots of the oil phase and the liposomal aqueous phase were removed.

In particular, the aqueous phase was extracted using heptane into which more than 98% of the lycopene was extracted. This extract was evaporated to dryness and the residue was dissolved in 200 μl isopropanol and analyzed by HPLC to determine the amount of lycopene present in the liquid and oil phase.

The concentration of lycopene in the liposome phase was calculated based on the procedure of Samuni and Barenholz [Samuni A. M. and Barenholz Y, Biol. Med. 22:1165–1174 (1996); Barenholz Y. et al. M. Biophys. J. 59:110–124 (1991)]. The following Table 4 summarizes the results obtained.

TABLE 4 lycopene concentration, solubility and partition coefficient (Kp)

| mμ | Crystalline | Power 92% Powder | Powder 75% | Oleoresin 6% | Tomato Con. |
| --- | --- | --- | --- | --- | --- |
| [C]o | 7.1200 | 6.7600 | 5.9200 | 6.1400 | 0.0660 |
| Oil phase | 0.1458 | 0.0495 | 0.1239 | 0.1785 | 0.0518 |
| Liposomal phase | 0.0001 | 0.0020 | 0.0062 | 0.0020 | 0.0048 |
| Insoluble lycopene | 6.9740 | 6.7084 | 5.7899 | 5.9594 | 0.0094 |
| Liposome/oil | 0.00095 | 0.0414 | 0.0497 | 0.0114 | 0.0920 |
| Kp Lip/Oil | 0.00952 | 0.4141 | 0.4972 | 0.1137 | 0.9199 |

Table 4 shows that more than 98% of the lycopene was insoluble in the aqueous phase. The liposome/oil Kp order is: powder 75%>powder 92%>oleoresin>>crystalline. The solubility of lycopene in the liposome lipid bilayer was of the same order as above.

These results show that lycopene has very low, if any, solubility in an aqueous phase and nevertheless may be carried by oil within the liposomes.

When lycopene encapsulated in MLV (ratio lipid/lycopene 10:1)) was stored for three weeks at 4° C. with soy oil covering them, the lycopene leaked from the liposome, and repartitioned in the oil phase, suggesting that lycopene can be transferred from the liposome to become bioavailable.

The stability of lycopene in liposomes formulated according to formulations E1 to E8 was determined, the results of which are shown in the following Table 5 (all formulations were stored as powder).

TABLE 5

Stability of lycopene in liposomes

| | mg powder/bottle | mg lycopene 75%/bottle | mg total lycopene/bottle | mg lycopene/bottle (HPLC) At time 0 | mg lycopene/bottle (HPLC) After 130 days | Decrease of lycopene content |
| --- | --- | --- | --- | --- | --- | --- |
| E1 | 31.8 | 2.86 | 2.145 | 1.83 | 1.59 | 13.1% |
| E2 | 31.8 | 2.86 | 2.145 | 1.83 | 1.70 | 7.1% |
| E3 | 32.3 | 1.54 | 1.155 | 1.13 | 0.74 | 34.5% |
| E4 | 32.3 | 1.54 | 1.155 | 1.135 | 0.94 | 17.2% |
| E5 | 32.9 | 1.06 | 0.795 | 0.697 | 0.65 | 6.7% |
| E6 | 32.9 | 1.06 | 0.795 | 0.769 | 0.67 | 12.9% |
| E7 | 32.3 | 0.63 | 0.472 | 0.493 | 0.42 | 14.8% |
| E8 | 32.3 | 0.63 | 0.472 | 0.581 | 0.48 | 17.4% |

In addition, the stability of different formulations (SO1–SO4) under different storage conditions was determined. Tables 6A and 6B compare the stability of different formulations, at time 0 (i.e. immediately after preparation and lyophilization, Table 6A) and after 1 year, with the following storage conditions (Table 6B, unless otherwise stated, storage temperature was −20° C.):

SO1: Formulation SO1 was stored either as a solution with isopropanol (preparation SO1(I)) or as a powder which was dissolved in cyclohexane before analysis (preparation SO1(II));

SO2: Formulation SO2 was stored either as a solution with isopropanol (preparation SO2(I)); as a powder dissolved with cyclohexane before analysis (preparation SO2 (II); or as a powder which one night before analysis was left at room temperature after which it was dissolved in cyclohexane for analysis (preparation SO2(III));

SO3: Formulation SO3 was stored either as a powder (−20° C.) dissolved in cyclohexane before analysis (preparation SO3(I)) or as a powder which one night before analysis was left at room temperature and then dissolved in cyclohexane for analysis (preparation SO3(II));

SO4: Formulation SO4 was stored either as a powder (−20° C.) dissolved in cyclohexane before analysis (preparation SO4(I)) or as a powder which one night before analysis was left at room temperature an only then dissolved in cyclohexane for analysis (preparation SO4(II).

The results presented in Table 6A and 6B show the lycopene concentration in the powder (lycopene in nmole/mg powder), lycopene concentration in the suspension formed just before analysis (lycopene μmole/ml), phospholipid (PL) concentration in the suspension (PL (μmole/ml) the mole-mole ratio between lycopene and lipid in the suspension (lycopene/lipid (mole/mole) and in Table 6B also the percent of degradation after storage for 1 year under the conditions defined above.

TABLE 6A

Stability of liposome encapsulated Lycopene 75% (at time 0)

| Preparation | Lycopene (nmole/mg powder) | Lycopene (μ mole/ml) | PL (μ mole/ml) | Lycopene/PL (mole/mole) |
|---|---|---|---|---|
| Saturated lycopene solution | | 0.33 ± 0.01 | | |
| SO1 | 0.040 ± 0.000002 | 0.0338 ± 0.008 | 18.43 ± 5.8 | 0.0019 ± 0.0001 |
| SO2 | 0.22 ± 0.000004 | 0.187 ± 0.03 | 14.3 ± 2.7 | 0.0132 ± 0.0003 |
| SO3 | 0.05 ± 0.000004 | 0.0373 ± 0.015 | 15.6 ± 4.57 | 0.0025 ± 0.0006 |
| SO4 | 0.04 ± 0.000006 | 0.03 ± 0.02 | 13.1 ± 4.1 | 0.0026 ± 0.0008 |

TABLE 6B

Stability of liposome encapsulated Lycopene 75% (after 1 year)

| Preparation | Lycopene (μ mole/ml) | Lycopene (nmole/mg powder) | PL (μ mole/ml liposome) | Lycopene/lipid (mole/mole) | Degradation (%) |
|---|---|---|---|---|---|
| Saturated lycopene solution | 0.34 ± 0.005 | | | | 1.50% |
| SO1 (I) | 0.0060 | 0.008 | | | 18.54% |
| SO1 (II) | 0.0170 | 0.020 | 18.33 ± 0.5 | 0.0003 | 7.56% |
| SO2 (I) | 0.0150 | 0.020 | | | 15.05% |
| SO2 (II) | 0.0025 | 0.003 | 18.48 ± 0.84 | 0.0001 | 58.84% |
| SO2 (III) | 0.006 ± 0.00086 | 0.003 | | | 55.36% |
| SO3 (I) | 0.0241 ± 0.00087 | 0.032 | 12.85 ± 0.91 | 0.0019 | 9.76% |
| SO3 (II) | 0.0285 | 0.018 | | | 10.1% |
| SO4 (I) | 0.0015 ± 0.00002 | 0.002 | 15.49 ± 0.94 | 0.00009 | 67.47% |
| SO4 (II) | 0.0024 | 0.003 | | | 64.08% |

As evident from the above results, the amount of lipids in the liposomal formulation did not substantially change with time while the amount of lycopene decreased with the formation of lycopene degradation products. The most stable powder was SO3, meaning, liposomes composed of S45: lycopene 75% with weight ratio of 45:1, stored after lyophilization as a powder. Formulations SO2 and SO4 were less stable.

In addition, the results show that the degree of purity of the lipid does not influence the stability of the formulation. In general, the formulation seems to be more stable when containing a greater amount of lipids. Further, the addition of other antioxidants, such as vitamin E may provide protection of lycopene from air oxidation.

Storage temperature had also an impact on the stability of the formulations. It was found that storage at room temperature resulted in a more rapid degradation of the lycopene as compared to storage at −20° C.

It should be noted that no BHT, an antioxidant, was added to the formulations and nevertheless, the formulations were found to be stable. This may suggest that the lipids protect lycopene oxidation and degradation, which would typically occur with free lycopene.

Additional experiments revealed that the stability of the SUV liposomes containing lycopene was similar to that of the MLV containing liposomes.

Photoprotective Properties of Liposomes Containing Lycopene

The photoprotective characteristics of the formulations SO1 to SO4 and E1–E8 were evaluated by measuring levels of IL-1α, and LDH release.

UV Induced Loss of Viability

Epidermal Equivalents were purchased from SkinEthic (Nice, France) and cultured in phenol free, hydrocortisone free media. Equivalents were topically treated with the different formulations at the indicated lycopene concentrations (0%, i.e. with the vehicle only, or at concentrations of 0.01%, 0.1% or 1%) 1 to 2 hours prior to irradiation with solar spectrum light using an Oriel solar simulator. Forty-eight hours post irradiation, the medium beneath each equivalent was collected and analyzed for secreted IL-1α by ELISA (Endogen). LDH level (Boehringer Mannheim) was measured immediately post irradiation and after 48 hours to determine the effect of treatment and UV exposure on cell viability.

Tables 7A, 7B and 7C summarize the results obtained by two repeated assays. The effect of ascorbic acid and lipoic acid on cell viability after irradiation was used as the control.

Tables 7A–7C-Protection Against UV Induced Loss of Viability

TABLE 7A

LDH Release

| Formulation | First assay | Second assay |
|---|---|---|
| SO1 | 58% protection with 1% | 41% protection with 1% |
| SO2 | 100% protection with 1% | 100% protection with 0.1% |
| SO3 | 58% protection with 1% | 58% protection with 0.1% |
| SO4 | 50% protection with 1% | 11% protection with 1% |
| Ascorbic acid | 100% protection with 0.01% | |

TABLE 7B

IL-1α release

| Formulation | First assay | Second assay |
|---|---|---|
| SO1 | 47% protection with 1% | 70% protection with 1% |
| SO2 | 100% protection with 1% | 100% protection with 0.1% |
| SO3 | 9% protection with 1% | 60% protection with 0.1% |
| SO4 | 25% protection with 1% | 50% protection with 1% |
| Ascorbic acid | 100% protection with 0.01% | |

TABLE 7C

Loss of viability (LDH)

| Formulation | LDH release |
|---|---|
| E1 | 100% protection with 1% |
| E2 | 100% protection with 1% |
| E3 | 100% protection with 1% |
| E4 | 100% protection with 1% |
| E5 | 100% protection with 1% |
| E6 | 100% protection with 1% |
| E7 | 100% protection with 1% |
| E8 | 100% protection with 1% |
| Lipoic Acid | 100% protection with 1% |

Figure 1A:
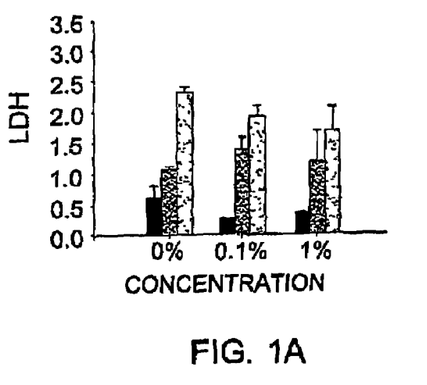
FIGS. 1A–1E are bar graphs showing IL-1α release (IL-1α (pg/ml)) obtained with topical compositions containing SO1 (FIG. 1A), SO2 (FIG. 1B), SO3 (FIG. 1C), SO4 (FIG. 1D) or with ascorbic acid as the control (FIG. 1E), at different lycopene concentrations: 0% (i.e. vehicle only), 0.1% and 1%. The level of release of IL-1α was measured at three different levels of UV radiation as determined by minimal erythemal dose (MED) levels.
Figure 1B:
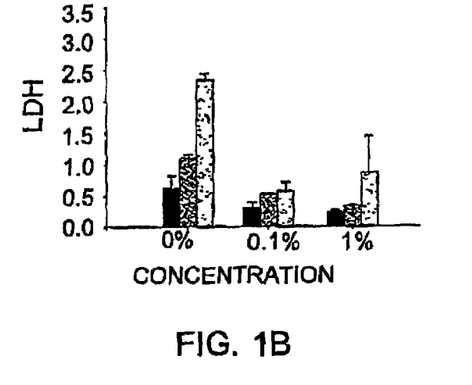
Figure 1C:
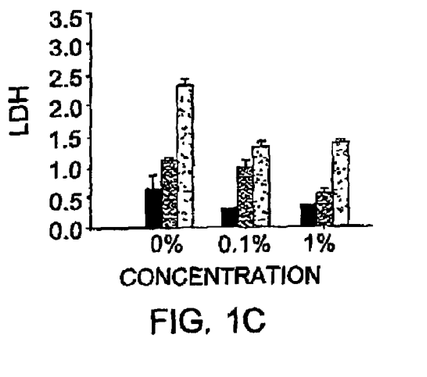
Figure 1D:
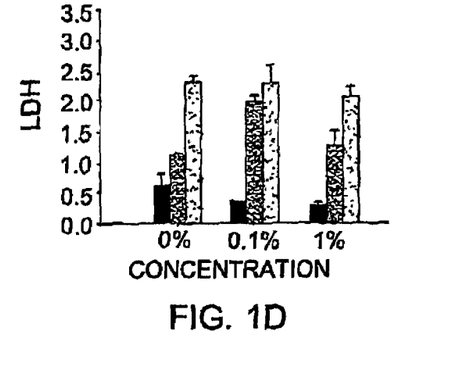
Figure 1E:
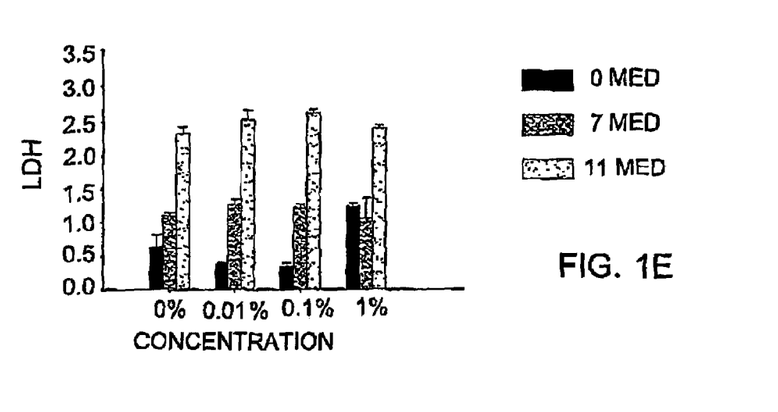
Figure 2A:
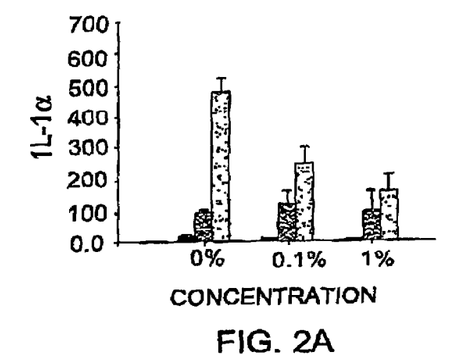
FIGS. 2A–2E are bar graphs showing LDH release (LDH) obtained with topical compositions containing SO1 (FIG. 2A), SO2 (FIG. 2B), SO3 (FIG. 2C), SO4 (FIG. 2D) or with ascorbic acid as the control (FIG. 2E), at different lycopene concentrations: 0% (i.e. vehicle only), 0.1% and 1%. The level of release of LDH release was measured at three different levels of UV radiation as determined by minimal erythemal dose (MED) levels.
Figure 2B:
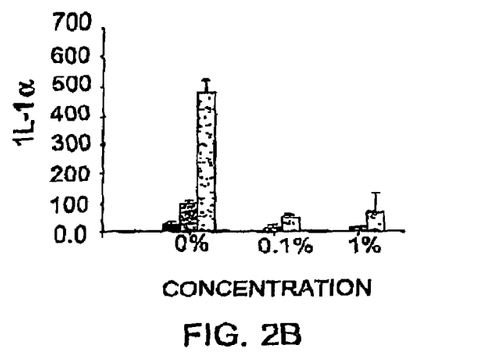
Figure 2C:
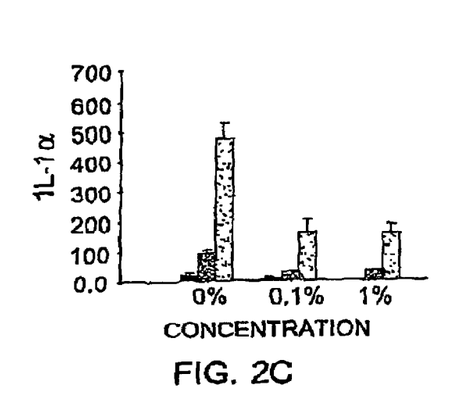
Figure 2D:
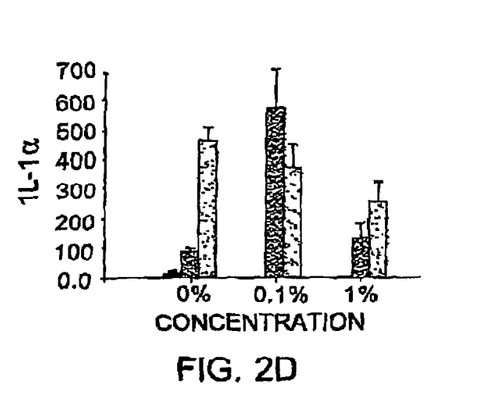
Figure 2E:
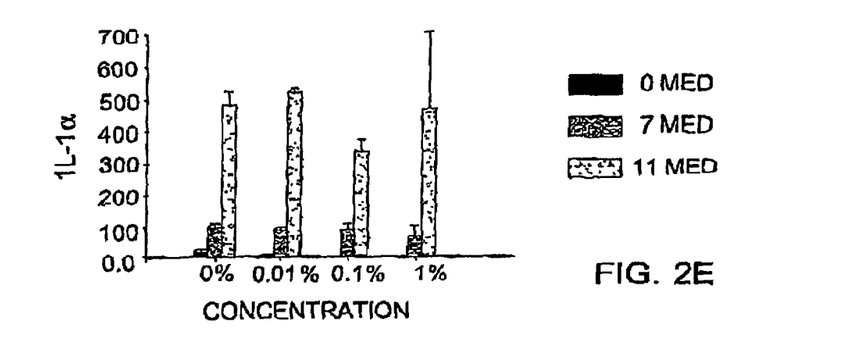

Similar results are presented in FIGS. 1 and 2. In particular, these Figures show levels of IL-1α and LDH release obtained when applying to the epidermal equivalents topical compositions comprising different concentrations of the liposomal lycopene. Vehicle containing ascorbic acid at different concentrations was used as the control.

These results presented in the above Tables and in the Figures suggest that low concentrations of the formulations disclosed by the present invention, are efficient in providing protection against UV radiation, as determined by the level of LDH and IL-1α release.

Oxazolone Induced Ear Edema

CD-1 Mice were induced with 3% oxazolone (Sigma) (30 mg/ml) made up in corn oil: acetone on a shaved abdomen. Five days later the mice were challenged with a 2% oxazolone (20 mg/ml) in acetone on the left ear, right ear was untreated. One hour after challenging, the formulations examined (E1–E8) in a 70% EtOH/30% propylene glycol vehicle were applied onto the left ear. After 24 hours the mice were sacrificed and 7 mm ear punches were taken. The ear punches were placed on a scale and the difference between the treated and untreated ears was measured.

The percent inhibition was calculated by comparing the means of each group to the vehicle group. The positive control was hydrocortisone. Table 8 summarizes the results.

TABLE 8

| Formulation | % inhibition |
|---|---|
| E1 | 60.2 |
| E2 | 56.1 |
| E3 | 34.8 |
| E4 | 60.0 |
| E5 | 75.8 |
| E6 | 79.2 |
| E7 | 58.3 |
| E8 | 85.5 |
| Hydrocortisone | 92.6 |

These results suggest that low concentrations of the formulations of the present invention are efficient in as agents against inflammation induced by oxazolone, particularly, the formulations E7 and E8.

While the invention has been described with reference to some preferred embodiments, it is understood that the words, which have been used herein, are words of description and illustration, rather man words of limitation. Changes may be made, within the purview of the appended claims, without departing from the scope and spirit of the invention in its aspects. Further, the content of the appended claims which define the present invention, should be read as included within the disclosure of the specification.

The invention claimed is:

1. A method for preparing a formulation comprising liposomes loaded with an effective amount of lycopene, the method comprising the steps of:
   a. dissolving a first powder of liposome-forming lipids in an organic solvent that freezes under lyophilization conditions;
   b. adding lycopene to the dissolved liposome-forming lipids obtained in step (a) to obtain a mixture of lycopene and liposome-forming lipids, and freeze-drying the solution to form a second dry powder; and
   c. rehydrating the second dry powder in an aqueous solution to yield liposomes loaded with lycopene.

2. The method of claim 1, wherein said liposome-forming lipids are phospholipids.

3. The method of claim 2, wherein said phospholipids are derived from egg yolk or soy oil.

4. The method of claim 1, wherein the solvent is cyclohexane.

5. The method of claim 1, wherein the weight ratio between said lycopene and the liposome-forming lipids in the resulting liposomal formulation is in the range of between 1:1 and 1:500.

6. The method of claim 1, wherein said lycopene is entrapped in the lipid bilayer of the liposome formed.

7. A formulation comprising liposomes loaded with an amount of a lycopene, the formulation being prepared by the method of claim 1.

8. The formulation of claim 7, wherein said liposomes are formed from lipids, the weight ratio between the lycopene and the liposome-forming lipids being in the range of between 1:1 and 1:500.

9. The formulation of claim 7, wherein said liposomes consist of a lipid bilayer and said lycopene is entrapped in said lipid bilayer.

10. The formulation of claim 7, wherein the liposome-forming lipids are phospholipids.

11. The formulation of claim 10, wherein said phospholipids are derived from egg yolk or from soy oil.

12. A pharmaceutical composition comprising a pharmaceutically or cosmetically effective amount of a formulation according to claim 7 and a pharmaceutically or cosmetically acceptable additive.

13. The composition of claim 7, wherein the formulation further comprises a pharmaceutically acceptable or cosmetically acceptable carrier.

14. The composition of claim 13, formulated for topical application to an individual's skin.

15. The composition of claim 14, in the form of a cream, a lotion, hydrogel or gel preparation.

16. The composition of claim 13, formulated for oral administration.

17. The composition of claim 16, in the form of a capsule.

18. The composition of claim 16, in the form of an edible wherein said formulation is in the form of a suspension.

19. The composition of claim 12, for the treatment of damage caused by the formation of singlet oxygen.

20. A therapeutic method for the treatment or prevention of damage caused by singlet oxygen, the method comprises providing an individual in need thereof a composition according to claim 7.

21. A pharmaceutical composition comprising a pharmaceutically or cosmetically effective amount of a formulation according to claim 8 and a pharmaceutically or cosmetically acceptable additive.

22. A pharmaceutical composition comprising a pharmaceutically or cosmetically effective amount of a formulation according to claim 9 and a pharmaceutically or cosmetically acceptable additive.

23. A pharmaceutical composition comprising a pharmaceutically or cosmetically effective amount of a formulation according to claim 10 and a pharmaceutically or cosmetically acceptable additive.

24. A pharmaceutical composition comprising a pharmaceutically or cosmetically effective amount of a formulation according to claim 11 and a pharmaceutically or cosmetically acceptable additive.

* * * * *